United States Patent [19]

Katsumata et al.

[11] Patent Number: 4,683,205
[45] Date of Patent: Jul. 28, 1987

[54] METHOD FOR TRANSFORMING MICROORGANISMS

[75] Inventors: Ryoichi Katsumata; Akio Ozaki, both of Machida; Tetsuo Oka, Yokohama; Akira Furuya, Kawasaki, all of Japan

[73] Assignee: Kyowa Hakko Kogyo Co., Ltd., Tokyo, Japan

[21] Appl. No.: 698,254

[22] Filed: Feb. 4, 1985

Related U.S. Application Data

[63] Continuation of Ser. No. 368,034, Apr. 13, 1982, abandoned.

[30] Foreign Application Priority Data

Apr. 17, 1981 [JP] Japan .................................. 56-58187

[51] Int. Cl.$^4$ .............................................. C12N 15/00
[52] U.S. Cl. .................................... 435/172.3; 935/52; 935/56; 935/58
[58] Field of Search ................. 435/172.3; 935/56, 55, 935/58, 52

[56] References Cited

PUBLICATIONS

Helling et al, Genetic Engineering Edited by Chakrabarty, CRC Press Inc. pp. 1, 13 & 14, (1978).
Fodor et al, Proc. Natl. Acad. Sci., USA, vol. 73, pp. 2147-2150, Jun. 1976.
Pappenheimer et al, Annual Review of Biochemistry, vol. 46, pp. 72, 73 & 92 (1977).
Kaneko et al, Agr. Biol. Chem. 43(4), pp. 867-868 (1979).
Freeman, Journal of Bacteriology vol. 61, pp. 675-688(1961).
Beggs, Nature, vol. 275, pp. 104-109 (1978).

*Primary Examiner*—Alvin E. Tanenholtz
*Attorney, Agent, or Firm*—Fitzpatrick, Cella, Harper & Scinto

[57] ABSTRACT

Disclosed is a method for transformation of microorganisms belonging to the genera Corynebacterium and Brevibacterium whereby a foreign DNA may be introduced into a host cell and autonomously replicated.

8 Claims, No Drawings

METHOD FOR TRANSFORMING MICROORGANISMS

This application is a continuation of application Ser. No. 368,034 filed Apr. 13, 1982, now abandoned.

BACKGROUND OF THE INVENTION

The present invention relates to a method for transformation of a microorganism and more specifically to a method whereby DNA such as a plasmid is introduced into a microorganism belonging to the genus Corynebacterium or Brevibacterium.

Recently, considerable attention has been devoted to genetic engineering technology wherein foreign genes are recombined with a vector DNA in vitro and the recombinant DNA is introduced into host cells. Such transformants are important as a means to produce the foreign DNA by autonomous replication of the vector and to endow the cell with valuable properties due to the presence of the foreign DNA.

Although most studies in this art have been developed using *Escherichia coli* as a host, efforts to establish recombinant DNA technology have been attempted on industrially useful microorganisms such as amylase-producing *Bacillus subtilis,* antibiotic-producing Actinomycetes and alcohol-producing yeasts. Recombinant DNA technology in any of the species of microorganisms requires essentially a vector, such as plasmids and phages, which can replicate autonomously in cells and a transformation method to introduce a recombinant DNA of the vector and a foreign DNA into the host cell. An applicable transformation method is, of course, a particularly important aspect for genetic engineering of industrially useful microorganisms such as those belonging to the genera Corynebacterium and Brevibacterium which are in use for the production of commercially significant products, for example glutamic acid, lysine and the like. To this end, a transformation method has now been developed suitable for microorganisms belonging to the genera Corynebacterium and Brevibacterium using the plasmid pCG4, isolated from Corynebacterium glutamicum 225-250, as a vector. The transformation procedure is, however, applicable to any plasmid and phage system.

Thus, the present invention provides a standard technique which enables the application of recombinant DNA technology to microorganisms belonging to the genus Corynebacterium or Brevibacterium, that is, to clone a desired gene of homologous or foreign origin.

SUMMARY OF THE INVENTION

The present invention provides a method wherein transformation of a microorganism belonging to the genus Corynebacterium or Brevibacterium can be readily carried out by introducing a DNA into a protoplast of the microorganism. The method comprises the steps of incubating protoplasts of a microorganism belonging to the genus Corynebacterium or Brevibacterium and a deoxyribonucleic acid (DNA) in the presence of polyethyleneglycol or polyvinylalcohol and a divalent metal cation to introduce the deoxyribonucleic acid into the protoplast; culturing the protoplast in a medium to regenerate the protoplasts to normal cells; and thereafter recovering a strain having a phenotype derived from the donor DNA.

DESCRIPTION OF THE INVENTION

Fundamentally, the method of the present invention comprises the following steps which are hereinafter described in detail:

(1) Prepraration of protoplasts of cultured cells;
(2) Transformation of the protoplast with a DNA;
(3) Regeneration of the protoplast to normal cells; and selection of a transformant.

(1) Preparation of protoplasts of cultured cells

The preparation of protoplasts is carried out by culturing a microorganism under conditions, which render it sensitive to lysozyme, a lytic enzyme, and treating the cultured cells with a lysozyme in a hypertonic solution to remove the cell walls. In order to render the microbial cells sensitive to lysozyme, reagents inhibiting the synthesis of cell walls are used. For example, microbial cells sensitive to lysozyme are obtained by adding, during the log phase of growth, an amount of penicillin which does not inhibit or sub-inhibits the growth and then continuing culturing for several generations.

For culturing, any medium wherein the microorganism propagates may be used. For example, a nutrient medium (NB) consisting of 20 g of powdered bouillon, 5 g of yeast extract and 1 liter of water (adjusted to pH 7.2) or a semi-synthetic medium (SSM) consisting of 10 g of glucose, 4 g of $NH_4Cl$, 2 g of urea, 1 g of yeast extract, 1 g of $KH_2PO_4$, 3 g of $K_2HPO_4$, 0.4 g of $MgCl_2.6H_2O$, 10 mg of $FeSO_4.7H_2O$, 0.2 mg of $MnSO_4.(4-6)H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin, 1 mg of thiamine hydrochloride and 1 liter of water (adjusted to pH 7.2) are appropriate. Microbial cells are inoculated in the medium and culturing is carried out with shaking. The optical density (OD) of the culture medium at 660 nm is measured with a colorimeter and penicillin, such as penicillin G, is added to the medium at an initial stage of the logarithmic growth phase (OD : 0.1–0.4) in a concentration of 0.1 to 2.0 U/ml. Culturing is then continued and at OD 0.3–0.5, the cells are harvested, followed by washing with SSM medium. The washed cells are resuspended in a suitable hypertonic medium such as PFM medium wherein 0.4M sucrose and 0.01M $MgCl_2.6H_2O$ are added to 2 fold diluted SSM medium, (pH adjusted to 7.0–8.5), and RCG medium consisting of 5 g of glucose, 5 g of casein hydrolysate, 2.5 g of yeast extract, 3.5 g of $K_2HPO_4$, 1.5 g of $KH_2PO_4$, 0.41 g of $MgCl_2.6H_2O$, 10 mg of $FeSO_4.7H_2O$, 2 mg of $MnSO_4.(4-6)H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin, 2 mg of thiamine hydrochloride, 135 g of sodium succinate and 1 liter of water and adjusted to pH 7.0–8.5. To the cell suspension, lysozyme to a final concentration of 0.2 to 10 mg/ml, is added and the mixture is allowed to react at a temperature of 30° to 37° C. Protoplast formation proceeds with time and is monitored with an optical microscope. The period required for the conversion of most cells to protoplasts depends on the concentration of penicillin during the sensitizing cultivation and the lysozyme used. The period is 3–24 hours under the conditions mentioned above.

Since protoplasts formed are destroyed under hypotonic conditions, the degree of the formation of protoplast is determined indirectly depending on the amount of normal cells surviving under hypotonic conditions.

Generally, the surviving normal cells are kept below $10^{-4}$ of lysozyme-treated normal cell.

The protoplasts prepared as above have colony-forming ability on a suitable hypertonic agar medium. As a regeneration medium, a nutrient medium, a semi-synthetic medium or a synthetic medium containing various amino acids, which contains 0.3 to 0.8M sodium succinate and 0.5 to 6% polyvinyl pyrrolidone with a molecular weight of 10,000 or 40,000 is preferably used. Generally, a semisynthetic RCGP medium wherein 3% polyvinyl pyrrolidone (molecular weight of 10,000) and 1.4% agar are added to RCG medium, pH adjusted to 7.2, is used. Regeneration is carried out at a temperature of 25° to 35° C. The cultivation time required for the regeneration of protoplasts depends upon the strain used but usually in 10 to 14 days a formed colony can be picked up. The efficiency of the regeneration of protoplasts on the RCGP medium also depends on the concentration of penicillin added during the cultivation and the lysozyme employed. The efficiency is generally $10^{-2}$–$10^{-4}$ cells per normal cell treated with lysozyme.

(2) Transformation of the protoplast with a DNA

Introduction of a DNA into a protoplast is carried out by mixing the protoplast and the DNA in a hypertonic solution containing polyethyleneglycol (PEG, average molecular weight: 1,540–6,000) or polyvinylalcohol (PVA, degree of polymerization: 500–1,500) and a divalent metal cation which stimulates uptake of the DNA. As a stabilizing agent, those generally used to protect protoplasts of other microorganisms such as sucrose and sodium succinate are also employed. PEG and PVA can be used in a final concentration of 5 to 60% and 1 to 20%, respectively. Divalent metal cations such as $Ca^{++}$, $Mg^{++}$, $Mn^{++}$, $Ba^{++}$ and $Sr^{++}$ are effectively used alone or in combination to a final concentration of 1 to 100 mM.

(3) Regeneration of the protoplast to normal cells and selection of a transformant Regeneration of the protoplast transformed with a DNA is carried out in the same way as mentioned above by spreading the protoplast on a hypertonic agar medium such as RCGP medium containing sodium succinate and polyvinyl pyrrolidone and incubating at a temperature wherein normal cells can grow, generally 25° to 35° C. Transformants are obtained by selection based on the phenotype derived from the donor DNA. The selection may be carried out simultaneously with the regeneration on the hypertonic agar medium or after regeneration.

Plasmid pCG4 used as an example of the donor DNA is a plasmid obtained from *Corynebacterium glutamicum* 225–250, FERM-P 5939, ATCC 31830 and having a molecular weight of about 19 megadaltons. Plasmid pCG4 carries a gene coding for resistance to streptomycin and spectinomycin. Therefore, transformants with the plasmid DNA can be conveniently recognized by the formation of colonies resistant to streptomycin and spectinomycin. Since spontaneously mutated microorganisms belonging to the genus Corynebacterium or Brevibacterium resistant to one of the antibiotics, streptomycin and spectinomycin, do not show cross resistance to the other, the transformant with plasmid pCG4 which assigns cross resistance can be readily distinguished. Transformants of a microorganism belonging to the genus Corynebacterium or Brevibacterium with plasmid pCG4 are obtained at a frequency of $10^{-6}$ to $10^{-4}$ per regenerated protoplast or $10^{-7}$ to $10^{-4}$ per regenerated normal cell. Since plasmids isolated from the cultured cells of these transformants give the same DNA fragments as plasmid pCG4 by the digestion of the restriction endonuclease Hind III, it is confirmed that the transformants carry plasmid pCG4.

Because a transformation method adopted in a microorganism is generally applicable to any DNA derived from different sources, the use of the transformation method of the present invention is not restricted to plasmid pCG4. That is, the present transformation method is applicable to other plasmid DNAs and phage DNAs autonomously replicable in microorganisms belonging to the genera Corynebacterium and Brevibacterium as well as chromosome DNAs which can be stabilized by the recombination after uptake into cells.

The transformation method of the present invention provides an essential means for the establishment of recombinant DNA technology in microorganisms belonging to the genus Corynebacterium or Brevibacterium useful for the industrial production of amino acids, nucleic acids and the like. The technology contributes to the increase of the yield of these useful products through stimulating the biosynthetic activities for producing them by cloning genes from the cells involved in the biosynthesis and by amplifying their genetic information.

Microbial strains obtained by the present transformation method using plasmid pCG4 are illustrated in Table 1. These strains have been deposited with the Fermentation Research Institute, Agency of Industrial Science and Technology, Japan and the American Type Culture Collection, U.S.A. under the accession numbers identified in the Table.

TABLE 1

| Recipient strain | Transformant with pCG4 | FERM-P No. | ATCC No. |
| --- | --- | --- | --- |
| *Corynebacterium glutamicum* ATCC 13761 | ATCC13761/ pCG4 | 5944 | 31836 |
| *Corynebacterium herculis* ATCC 13868 | ATCC13868/ pCG4 | 5941 | 31837 |
| *Brevibacterium flavum* ATCC 14067 | ATCC14067/ pCG4 | 5942 | 31838 |
| *Brevibacterium lactofermentum* ATCC 13655 | ATCC13655/ pCG4 | 5943 | 31839 |

Certain specific embodiments of the invention are illustrated by the following representative examples reflecting actual experimental data.

EXAMPLE 1

Isolation of plasmid:

In this step, plasmid pCG4 is isolated and purified from the cultured cells of *Corynebacterium glutamicum* 225–250 carrying plasmid pCG4.

*Corynebacterium glutamicum* 225–250 is cultured with shaking in NB medium at 30° C. for 18 hours. Then, 5 ml of the seed culture is inoculated into 400 ml of a semisynthetic medium (SSM) and culturing is carried out with shaking at 30° C. The optical density (OD) at 660 nm is measured using a Tokyo Koden colorimeter and at OD 0.2, penicillin G is added to the broth to a final concentration of 0.5 U/ml. Culturing is then continued at 30° C. to OD about 0.6.

Cells are then recovered from the culture broth, washed with TES buffer solution (pH 8.0) consisting of 0.03M tris(hydroxyme)aminomethane (Tris), 0.005M disodium ethylenediamine tetraacetate (EDTA) and 0.05M NaCl and supended in a lysozyme solution (pH 8.0) consisting of 25% sucrose, 0.1M NaCl, 0.05M Tris and 0.8 mg/ml egg white lysozyme 6× crystallized (Seikagaku Kogyo Co.) to make up 10 ml of a suspension. The suspension is incubated at 37° C. for 4 hours. Then, 2.4 ml of 5M NaCl, 0.6 ml of 0.5M EDTA (pH 8.5) and 4.4 ml of a mixed solution of 4% sodium laurylsulfate and 0.7M NaCl are added successively to the reaction suspension. After the mixture is stirred slowly, it is kept on an ice water bath for 15 hours. The whole lysate is then put into a centrifugation tube and centrifuged under 69,400 x g at 4° C. for 60 minutes to obtain a supernatant fluid. To the supernatant, 10% by weight of polyethyleneglycol 6,000 is added. After the mixture is stirred slowly to dissolve it, it is kept on an ice water bath. After 16 hours, the mixture is centrifuged at 1,500×g for 10 minutes to obtain a pellet. The pellet is redissolved in 5 ml of TES buffer solution and 2.0 ml of 1.5 mg/ml ethidium bromide is added. Then, cesium chloride is added to the mixture with gentle stirring to adjust the density to 1.580. The solution is then subjected to centrifugation under 105,000×g at 18.0° C. for 48 hours. After the density gradient centrifugation, a circular DNA closed with a covalent bond is detected by UV irradiation as a high density band located in the lower part of the centrifugation tube. The band is taken out from the side of the tube with an injector to obtain a fraction containing plasmid pCG4. The fraction is treated five times with an equal amount of cesium chloride saturated-isopropyl alcohol solution consisting of 90% by volume of isopropyl alcohol and 10% TES buffer solution to remove the ethidium bromide. Then, the residue is subjected to dialysis against TES buffer solution, whereby 15 μg of plasmid pCG4 is recovered.

Transformation of *Corynebacterium glutamicum* with plasmid pCG4:

In this step, *Corynebacterium glutamicum* ATCC 13761 is cultured with shaking in NB medium at 30° C. for 16 hours and then 0.075 ml of the seed culture is inoculated in 7.5 ml of SSM medium in an L-tube. Culturing is carried out at 30° C. with a Monod type shaker. The optical density (OD) at 660 nm is measured with a Tokyo Koden colorimeter and at OD 0.15, penicillin G is added to a final concentration of 0.5 U/ml. Culturing is continued to OD about 0.5. Cells are recovered from the culture broth, washed with SSM and suspended in 2 ml of PFM medium (pH 7.6). A small part of the suspension is diluted with NB medium, spread on an NB agar medium containing 1.8% agar, and incubated at 30° C. for 2 days to determine the number of cells subjected to the lysozyme treatment. This number is found to be $1.2 \times 10^9$/ml.

Cells harvested from the remaining suspension are resuspended at the original density in PFM medium (pH 7.6) containing 500 μg/ml lysozyme solution and incubated at 30° C. The PFM medium is sterilized with a milipore filter. After 12 hours, it is judged with an optical microscope that most cells are converted to protoplasts. The protoplasts are recovered by centrifugation at 2,500×g for 10 minutes and suspended in 2.0 ml of PFM medium (pH 7.6). The suspension is subjected to centrifugation and washing and then the protoplast is resuspended in 20 ml of the same medium to make up a protoplast suspension. A part of the suspension is diluted with RCG medium and spread on an RCGP agar medium and another part is diluted with NB medium and spread on an NB agar medium. Incubation is carried out at 30° C. and the number of colonies which can grow under the hypertonic condition and the hypotonic condition are counted, respectively. Colonies formed under hypotonic condition are counted after 2 days. The number of colonies does not increase with subsequent cultivation. Colonies formed under hypertonic condition are counted after 14 days, and thereafter any increase in number of colonies is not observed. In the present example, the ratio of colonies formed under the hypotonic condition, i.e. colonies resistant to osmotic shock is $3.1 \times 10^{-4}$ per cell subjected to the lysozyme treatment and that under the hypertonic condition, i.e. regenerated cells is $1.7 \times 10^{-2}$.

Transformation is carried out using the protoplast prepared above. For this step, 0.5 ml of the protoplast cells is put into a small tube and centrifuged at 2,500×g for five minutes. The precipitate is suspended in 1.0 ml of TS buffer solution (pH 7.5) consisting of 0.05M tris(-hydroxymethyl)aminomethane (Tris) and 0.4M sucrose and containing 30 mM each of divalent metal cations which are used in the following transformation, and subjected to centrifugation and washing. Then, 0.1 ml of the same buffer solution is added to the deposited protoplasts and the mixture is stirred slowly. To the suspension is added 0.2 μg of plasmid in 0.1 ml of the TS solution containing 30mM each of divalent metal cations. Then, 0.8 ml of TS buffer solution containing 30 mM each of divalent metal cations and 20% PEG 6,000 or 10% PVA (degree of polymerization : 500) is added and mixed slowly. After 3 minutes, 2 ml of RCG medium is added and the mixture is centrifuged at 2,500×g for 5 minutes. The supernatant is removed and the precipitated protoplast is suspended with gentle shaking in 1 ml of RCG medium. The suspension is allowed to stand at 30° C. After 2 hours, the suspension is sufficiently diluted and a portion of the diluent is spread on an RCGP agar medium containing 400 μg/ml spectinomycin. To determine the number of cells capable of forming colonies, a portion of a highly diluted suspension is also spread on an RCGP agar medium. After incubating at 30° C. for 14 days, colonies formed are counted. As controls, systems without plasmid pCG4, PEG or divalent metal cations are run in parallel.

Then, 5 to 100 colonies formed on the RCGP medium containing spectinomycin are spread on an NB agar medium containing 12.5 μg/ml streptomycin and culturing is carried out at 30° C. for 2 days to examine the cross resistance to streptomycin.

Two cross resistant strains are picked up at random and the presence of plasmid pCG4 therein is confirmed in the same manner as above described. The results are illustrated in Table 2.

TABLE 2

| Transformation treatment | pCG4 | Frequency of colonies resistant to spectinomycin* | Property of the resistant strain to spectinomycin** | |
|---|---|---|---|---|
| | | | Cross resistance to streptomycin | pCG4 |
| TS + PEG + CaCl$_2$ | — | $3.7 \times 10^{-7}$ | −(5/5) | −(2/2) |
| TS | + | $4.1 \times 10^{-7}$ | −(7/7) | −(2/2) |
| TS + PEG | + | $4.2 \times 10^{-6}$ | +(3/10) −(7/10) | +(2/2) |
| TS + CaCl$_2$ | + | $1.3 \times 10^{-6}$ | +(2/10) −(8/10) | +(2/2) |
| TS + PEG + CaCl$_2$ | + | $5.1 \times 10^{-4}$ | +(100/100) | +(2/2) |

TABLE 2-continued

| Transformation treatment | pCG4 | Frequency of colonies resistant to spectinomycin* | Property of the resistant strain to spectinomycin** | |
|---|---|---|---|---|
| | | | Cross resistance to streptomycin | pCG4 |
| TS + PEG + MgCl$_2$ | + | 1.3 × 10$^{-4}$ | +(100/100) | +(2/2) |
| TS + PEG + MnCl$_2$ | + | 8.8 × 10$^{-5}$ | +(100/100) | +(2/2) |
| TS + PEG + BaCl$_2$ | + | 3.4 × 10$^{-4}$ | +(100/100) | +(2/2) |
| TS + PEG + SrCl$_2$ | + | 2.9 × 10$^{-4}$ | +(100/100) | +(2/2) |
| TS + PVA + CaCl$_2$ | + | 3.7 × 10$^{-4}$ | +(100/100) | +(2/2) |

*Frequency per cell being able to form colonies under hypertonic condition (i.e. regenerated cell).
**The number of tested cells (denominator) and those of negative (−) or positive (+) cells (numerator) are shown in parentheses.

The strains resistant to spectinomycin obtained without plasmid pCG4 have no cross resistance to streptomycin and are free of plasmid pCG4. The strains obtained in the presence of plasmid pCG4 as well as PEG or divalent metal cations or both have cross resistance to streptomycin. Since the plasmids isolated from these strains give the same DNA fragments as pCG4 after digestion with a restriction enzyme, Hind III, and agarose gel electrophoresis, these strains are identified as transformants carrying plasmid pCG4.

EXAMPLE 2

Transformation of the microorganisms belonging to the genera Corynebacterium and Brevibacterium with plasmid pCG4:

In this example, transformation of *Corynebacterium glutamicum* ATCC 13761, *Corynebacterium herculis* ATCC 13868, *Brevibacterium flavum* ATCC 14067 and *Brevibacterium lactofermentum* ATCC 13655 are carried out as follows: The culturing of cells and preparation of protoplasts are carried out in the same manner as in Example 1 except that lysozyme treatment is continued for 14 hours in an RCG medium. In the transformation step, a solution containing 20% PEG 6,000, 30 mM calcium chloride and TS buffer solution wherein sucrose is replaced with 0.5M sodium succinate is used. A system without plasmid pCG4 is also used as a control.

Protoplasts obtained by the same treatments as in Example 1 are suspended in 1 ml of RCG medium and diluted immediately with RCG medium. The diluent is spread on an RCGP agar medium and incubated at 30° C. for 12 days.

Regenerated cells on the agar medium are scraped with a platinum loop and suspended in 2 ml of NB medium. The suspension is then diluted and spread on an NB agar medium containing 12.5 μg/ml streptomycin. At the same time, a highly diluted suspension is spread on an NB agar medium in order to count viable cells in the suspension. These agar media are incubated at 30° C. for 2 days and colonies formed are counted.

Colonies formed on the NB agar medium containing streptomycin are picked up and replica-plated on an NB agar medium containing 100 μg/ml spectinomycin followed by incubation at 30° C. for 2 days to examine the cross resistance to spectinomycin.

Three cross resistant strains for each species are picked up at random and the plasmids are isolated as in Example 1. The plasmids are digested with a restriction endonuclease, Bam HI, and subjected to agarose gel electrophoresis to determine the presence of the same DNA fragments as those derived from plasmid pCG4.

The results are illustrated in Table 3. Some differences are recognized depending on the species. Streptomycin resistant strains are obtained more frequently (10$^{-7}$ to 10$^{-4}$ per survival of cells) in the system with plasmid pCG4 than in the system without plasmid pCG4. Since all streptomycin resistant strains tested show cross resistance to spectinomycin and carry plasmid pCG4, these strains are recognized as transformants with plasmid pCG4.

TABLE 3

| Recipient | pCG4 | Frequency of colonies resistant to streptomycin* | Property of the strain resistant to streptomycin** | |
|---|---|---|---|---|
| | | | Cross resistance to spectinomycin | pCG4 |
| *Corynebacterium glutamicum* ATCC 13761 | − | <5.0 × 10$^{-9}$ | | |
| | + | 5.6 × 10$^{-5}$ | +(20/20) | +(3/3) |
| *Corynebacterium herculis* ATCC 13868 | − | 2.3 × 10$^{-8}$ | −(3/3) | |
| | + | 1.0 × 10$^{-4}$ | +(20/20) | +(3/3) |
| *Brevibacterium flavum* ATCC 14067 | − | 1.1 × 10$^{-8}$ | −(5/5) | |
| | + | 7.7 × 10$^{-7}$ | +(20/20) | +(3/3) |
| *Brevibacterium lactofermentum* ATCC 13655 | − | 3.0 × 10$^{-9}$ | (2/2) | |
| | + | 2.1 × 10$^{-7}$ | +(20/20) | +(3/3) |

*Frequency per regenerated cell.
**The number of cells tested (denominator) and those of negative (−) or positive (+) cells (numerator) are illustrated in parentheses.

What is claimed is:

1. A method for transforming microorganisms, which comprises:
    (1) selecting a microbial strain of one of the group of genera consisting of Corynbacterium and Brevibacterium;
    (2) incubating protoplasts of said microbial strain and a donor deoxyribonucleic acid selected from the group consisting of chromosomal DNAs which are stabilized after cellular introduction by recombination and plasmids in the presence of polyethylene glycol or polyvinylalcohol and at least one divalent metal cation whereby to introduce said donor deoxyribonucleic acid into said protoplasts;
    (3) regenerating said protoplasts by culturing in a hypertonic nutrient medium; and
    (4) thereafter recovering a transformed strain having a phenotype derived from said donor deoxyribonucleic acid.

2. A method according to claim 1 wherein said divalent metal cation is selected from the group consisting of calcium, magnesium, manganese, barium and strontium.

3. A method according to claim 2 wherein said divalent metal cation is present at a concentration of from about 1 to 100 mM.

4. A method according to claim 1 wherein said polyethyleneglycol is present at a concentration of from 5 to 60%.

5. A method according to claim 1 wherein said polyvinylalcohol is present at a concentration of from 1 to 20%.

6. A method according to claim 1 wherein said donor deoxyribonucleic acid is a plasmid or a phage.

7. A method according to claim 6 wherein said plasmid is derived from a microorganism belonging to the genus Corynebacterium or Brevibacterium.

8. A method according to claim 7 wherein said plasmid is plasmid pCG4.

* * * * *

UNITED STATES PATENT AND TRADEMARK OFFICE
CERTIFICATE OF CORRECTION

PATENT NO. : 4,683,205
DATED : July 28, 1987
INVENTOR(S) : RYOICHI KATSUMATA, ET AL.

It is certified that error appears in the above-identified patent and that said Letters Patent is hereby corrected as shown below:

Column 5, line 1, "(hydroxyme)" should read --(hydroxymethyl)--.

Column 8, line 25, "(2/2)" should read --  -( 2/2 )  --.

Column 8, line 35, "Corynbacterium" should read
    --Corynebacterium--.

Signed and Sealed this

Fifth Day of January, 1988

Attest:

DONALD J. QUIGG

Attesting Officer            Commissioner of Patents and Trademarks